United States Patent [19]

Riebel et al.

[11] 3,966,920

[45] June 29, 1976

[54] O,S-DIALKYL-O-(2-CYANOPHENYL)-THIONOTHIOLPHOSPHORIC ACID ESTERS AND INSECTICIDAL AND ACARICIDAL COMPOSITIONS AND METHOD

[75] Inventors: Hans-Jochem Riebel, Wuppertal; Ingeborg Hammann, Cologne; Wilhelm Stendel, Wuppertal, all of Germany

[73] Assignee: Bayer Aktiengesellschaft, Leverkusen, Germany

[22] Filed: Dec. 4, 1974

[21] Appl. No.: 529,660

[30] Foreign Application Priority Data
Dec. 5, 1973 Germany.......................... 2360548

[52] U.S. Cl.............................. 424/210; 260/940
[51] Int. Cl.² ....................... A01N 9/36; C07F 9/18
[58] Field of Search ............ 260/940, 964; 424/210

[56] References Cited
UNITED STATES PATENTS
3,825,636   7/1974   Kishino et al................... 260/940 X FOREIGN PATENTS OR APPLICATIONS
255,279   11/1964   Australia............................. 260/940
98,101    2/1964   Denmark.............................. 260/964

*Primary Examiner*—Richard L. Raymond
*Attorney, Agent, or Firm*—Burgess, Dinklage & Sprung

[57] ABSTRACT

O,S-Dialkyl-O-(2-cyanophenyl)-thionothiolphosphoric acid esters of the formula

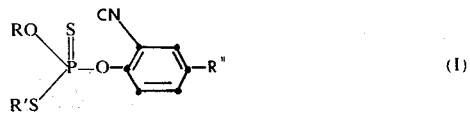

in which
R and R' each independently is alkyl with 1 to 6 carbon atoms, and
R" is hydrogen or bromine,
which possess insecticidal and acaricidal properties.

9 Claims, No Drawings

O,S-DIALKYL-O-(2-CYANOPHENYL)-THIONO-THIOLPHOSPHORIC ACID ESTERS AND INSECTICIDAL AND ACARICIDAL COMPOSITIONS AND METHOD

The present invention relates to and has for its objects the provision of particular new O,S-dialkyl-O-(2-cyanophenyl)-thionothiolphosphoric acid esters, optionally bromo-substituted in the 4-position on the phenyl ring, which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has been disclosed in Belgian Patent Specification 627,817 that 2-cyanophenylthiophosphoric acid esters, for example O,O-diethyl-O-(2-cyanophenyl)-thionophosphoric acid ester (Compound A), possess good insecticidal and acaricidal properties. However, these compounds have a high toxicity to warm-blooded animals.

The present invention provides 2-cyanophenyldithiophosphoric acid esters of the general formula

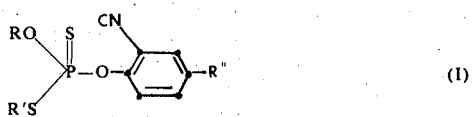

in which

R and R' each independently is alkyl with 1 to 6 carbon atoms, and

R'' is hydrogen or bromine.

R and R', which may be straight chain or branched lower alkyl, preferably each have 1 to 4 carbon atoms. Compounds wherein R' has at least as many carbon atoms as R, especially where R is ethyl and R' is n-propyl, are particularly preferred.

Surprisingly, the 2-cyanophenyldithiophosphoric acid esters (I) according to the invention whilst having a very low toxicity to warm-blooded animals, exhibit a better insecticidal and acaricidal action than previously known compounds. The compounds according to the invention thus represent a genuine enrichment of the art.

The invention also provides a process for the production of a 2-cyanophenyldithiophosphoric acid ester of the formula (I) in which a dithiophosphoric acid ester-halide of the general formula

in which

R and R' have the abovementioned meanings, and

Hal s halogen, preferably chlorine, is reacted with a 2-cyanophenol of the general formula

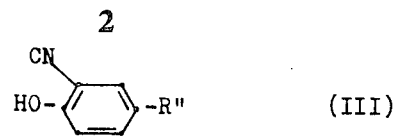

in which

R'' has the abovementioned meaning optionally in the presence of an acid acceptor, or in the form of an alkali metal salt, alkaline earth metal salt or ammonium salt, and optionally in the presence of a solvent.

If, for example, O-ethyl-S-sec.-butyl-thionothiolphosphoric acid ester-chloride and 2-cyanophenol are used, the course of the reaction can be represented by the following equation:

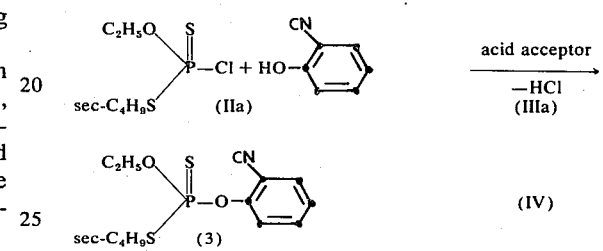

The O,S-dialkly-thionothiolphosphoric acid ester halides (II) to be used as starting materials can be prepared by conventional methods, e.g. USSR Patent Specification 184,863 and published Japanese Patent Application 5536/72.

The following are specific examples of such compounds: O-ethyl-S-n-propyl-, O-ethyl-S-n-butyl-, O-ethyl-S-sec.-butyl, O-ethyl-S-tert.-butyl, O-n-propyl-S-n-propyl-, O-n-propyl-S-sec.-butyl-, O-n-propyl-S-ios-butyl-, O-n-propyl-S-tert.-butyl-, O-iso-propyl-S-n-butyl- and O-iso-propyl-S-sec.-butyl-thionothiolphosphoric acid ester chloride.

The cyanophenols (III) which are also used as starting materials are described in the literature and are obtainable by conventional methods, e.g. Berichte der duetschen Chemischen Gesellschaft 26 (1893) 2623 and 31 (1898) 3042

The reaction according to the present invention is preferably carried out in the presence of a solvent which term includes a mere diluent. Practically all inert organic solvents can be employed for this purpose. These include, in particular, aliphatic and aromatic optionally chlorinated hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, dimethylaniline, dimethylbenzylamine and pyridine.

The reaction temperature can be varied within a wide range. In general, the reaction is carried out at 0° to 100°, preferably at 15° to 60°C.

The reaction is in general allowed to take place under normal pressure.

To carry out the process, the starting materials are in most cases employed in equimolar ratio. An excess of one or other reactant seems to produce no significant advantages. The reaction is in general carried out in a solvent in the presence of an acid acceptor and is completed by stirring for between 1 and several hours at elevated temperatures. The mixture is then cooled and poured into an organic solvent, for example toluene. The organic phase may then be washed with saturated sodium carbonate solution and subsequently with water and dried, the solvent distilled off under reduced pressure and the residue purified by "slight distillation".

Some of the new compounds are obtained in the form of oils which in most cases cannot be distilled without decomposition but can be freed from remaining volatile impurities by so-called "slight distillation", that is to say prolonged heating under reduced pressure to moderately elevated temperatures, and they can be purified in this way. They are characterized by their refractive indexes.

As already mentioned, the 2-cyanophenyldithiophosphoric acid esters (I) according to the invention are distinguished by a very good insecticidal and acaricidal activity coupled with very low toxicity to warm-blooded animals. They possess a good action both against sucking and biting insects and against mites (Acarina). For this reason, the compounds according to the invention can be employed with success as pesticides in plant protection, in the hygiene field and in the field of protection of stored products and/or in the veterinary medicine field against animal ectoparasites.

To the sucking insects there belong, in the main, aphids (Aphididae) such as the green peach aphid (*Myzus persicae*), the beam aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoëa*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium panicuem*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (Periplaneta americana), Madeira cockroach (*Leucophaea* or *Rhyparobia maderae*), oriental cockraoch (*Blatta orientalis*), the giant cockroach (*Blaberus giganteus*) and the black giant cockroach (*blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophilia melanogaster*), the Mediterranean fruit fly (*Cerattis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*anopheles stephensi*).

With the mites (Acari) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsoneimids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the compounds of the invention are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (.e.g glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen in Table 1.

Table 1

(Plutella test)

| Active compound | Active compound concentration in % by weight | Degree of destruction in % after 3 days. |
|---|---|---|
| (C₂H₅O)(C₂H₅O)P(=S)–O–[cyclohexenyl-CN] (A) | 0.1<br>0.01<br>0.001 | 100<br>100<br>0 |
| (n-C₃H₇S)(C₂H₅O)P(=S)–O–[phenyl-CN] (2) | 0.1<br>0.01<br>0.001 | 100<br>100<br>95 |
| (n-C₃H₇S)(C₂H₅O)P(=S)–O–[phenyl-Br,CN] (1) | 0.1<br>0.01<br>0.001<br>0.0001 | 100<br>100<br>100<br>100 |

EXAMPLE 2

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of aphids were killed.

The active compounds, the concentration of the active compounds, the evaluation times and the results can be seen in Table 2.

Table 2

(Myzus test)

| Active compound | Active compound concentration in % by weight | Degree of destruction in % after 3 days. |
|---|---|---|
| (C₂H₅O)(C₂H₅O)P(=S)–O–[phenyl-CN] (A) | 0.1<br>0.01<br>0.001 | 100<br>50<br>0 |
| (n-C₃H₇S)(C₂H₅O)P(=S)–O–[phenyl-CN] (2) | 0.1<br>0.01<br>0.001 | 100<br>100<br>95 |
| (n-C₃H₇S)(C₂H₅O)P(=S)–O–[phenyl-Br,CN] (1) | 0.1<br>0.01<br>0.001<br>0.0001 | 100<br>100<br>100<br>50 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen in Table 3.

Table 3

(Tetranychus test/resistant)

| Active Compound | Active compound concentration in % by weight | Degree of destruction in % after 2 days |
|---|---|---|
| (C₂H₅O)(C₂H₅O)P(=S)–O–[phenyl-CN] (A) | 0.1 | 0 |
| (n-C₃H₇S)(C₂H₅O)P(=S)–O–[phenyl-CN] (2) | 0.1<br>0.01 | 100<br>85 |
| (n-C₃H₇S)(C₂H₅O)P(=S)–O–[phenyl-Br,CN] (1) | 0.1<br>0.01 | 99<br>45 |

EXAMPLE 4

Test with parasitic fly larvae
Solvent: 35 parts by weight of ethylene polyglycol monomethyl ether
35 parts by weight of nonylphenol polyglycol ether To produce a suitable preparation of active compound, 30 parts by weight of the active substance in question were mixed with the stated amount of solvent which contained the abovementioned proportion of emulsifier and the concentrate thus obtained was diluted with water to the desired concentration.

About 20 fly larvae (*Lucilia cuprina*) were introduced into a test tube which contained approximately 2 cm³ of horse muscle. 0.5 ml of the preparation of active compound was applied to this horse meat. After 24 hours, the degree of destruction in % was determined. 100% means that all larvae had been killed and 0% means that no larvae had been killed.

The results obtained can be seen in Table 4.

Table 4

| Active compound | (Test with parasitic fly larvae/Lucilia cuprina, resistant) | |
|---|---|---|
| | Active compound concentration in ppm by weight | Degree of destruction in % |
| 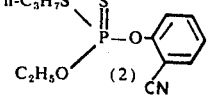 (2) | 100 | 100 |
| | 30 | 100 |
| | 10 | 100 |
| | 3 | 100 |
| | 1 | 100 |
| | 0.3 | 0 |

EXAMPLE 5

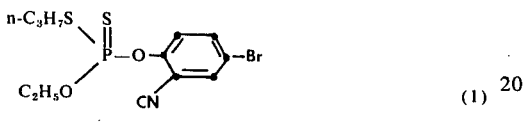 (1)

21.8 g (0.1 mole) of O-ethyl-S-n-propyl-thionothiolphosphoric acid diester chloride were added dropwise to a mixture of 19.8 g (0.1 mole) of 2-cyano-4-bromophenol and 14.5 g (0.105 mole) of potassium carbonate in 200 ml of acetonitrile. The mixture was allowed to react for a further 3 hours at 50° to 60°C and was then cooled, and the batch was poured into 500 ml of toluene. The organic phase was washed with saturated sodium carbonate solution and with water and dried over sodium sulfate. The solvent was then evaporated off under reduced pressure and the residue was subjected to "slight distillation". 25 g (65.5% of theory) of O-ethyl-S-n-propyl-O-(2-cyano-4-bromophenyl)-thionothiolphosphoric acid ester were obtained in the form of a yellow oil of refractive index $n_D^{21}$= 1.5796.

EXAMPLE 6

The following compound was prepared by the method of Example 5:

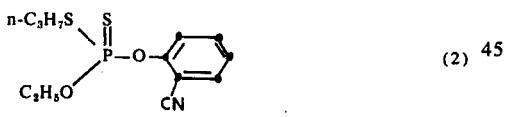 (2)

Refractive index: $n_D^{22}$= 1.5558 Yield: 68% of theory.
Other compounds which can be similarly prepared include:
O-ethyl-S-n-butyl-O-(2-cyanophenyl)-thionothiolphosphoric acid ester,
O-ethyl-S-sec.-butyl-O-(2-cyano-4-bromophenyl)thionothiolphosphoric acid ester,
O-ethyl-S-tert.-butyl-O-(2-cyanophenyl)-thionothiolphosphoric acid ester,
O-n-propyl-S-n-propyl-O-(2-cyano-4-bromophenyl)-thionothiolphosphoric acid ester,
O-n-propyl-S-sec.-butyl-O-(2-cyanophenyl)thionothiolphosphoric acid ester,
O-n-propyl-S-iso-butyl-O-(2-cyano-4-bromophenyl)-thionothiolphosphoric acid ester,
O-n-propyl-S-tert.-butyl-O-(2-cyano-4-bromophenyl)-thionothiolphosphoric acid ester,
O-iso-propyl-S-n-butyl-O-(2-cyano-4-bromophenyl)thionothiolphosphoric acid ester,
O-iso-propyl-S-sec.-butyl-O-(2-cyanophenyl)-thionothiolphosphoric acid ester,
O-iso-butyl-S-methyl-O-(2-cyano-4-bromophenyl)-thionothiolphosphoric acid ester,
O-methyl-S-n-propyl-O-(2-cyanophenyl)-thionothiolphosphoric acid ester,
and the like.

It will be appreciated that the instant specification and examples are set forth by way of illustration and not limitation, and that various modifications and changes may be made without departing from the spirit and scope of the present invention.

What is claimed is:

1. A 2-cyanophenyldithiophosphoric acid ester of the formula

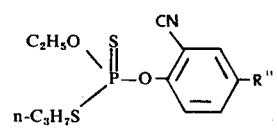

in which R'' is hydrogen or bromine.

2. The compound according to claim 1 wherein such compound is O-ethyl-S-n-propyl-O-(2-cyano-4-bromophenyl)-thionothiolphosphoric acid ester of the formula

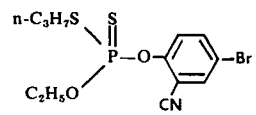

3. The compound according to claim 1 wherein such compound is O-ethyl-S-n-propyl-O-(2-cyanophenyl)-thionothiolphosphoric acid ester of the formula

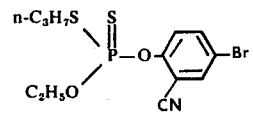

4. An insecticidal or acaricidal composition containing as active ingredient an insecticidally or acaricidally effective amount of a compound according to claim 1 in admixture with a diluent.

5. A composition according to claim 4 wherein such compound is O-ethyl-S-n-propyl-O-(2-cyano-4-bromophenyl)-thionothiolphosphoric acid ester.

6. A composition according to claim 4 wherein such compound is O-ethyl-S-n-propyl-O-(2-cyanophehyl)thionothiolphosphoric acid ester.

7. A method of combating insect or acarid pests which comprises applying to the pests or a habitat thereof an insecticidally or acaricidally effective amount of a compound according to claim 1.

8. The method of claim 7 wherein such compound is O-ethyl-S-n-propyl-O-(2-cyano-4-bromophenyl)-thionothiolphosphoric acid ester.

9. The method of claim 7 wherein such compound is O-ethyl-S-n-propyl-O-(2-cyanophenyl)-thionothiolphosphoric acid ester.

* * * * *

UNITED STATES PATENT OFFICE
CERTIFICATE OF CORRECTION

Patent No. 3,966,920  Dated June 29, 1976

Inventor(s) Hans-Jochem Riebel et al.

It is certified that error appears in the above-identified patent and that said Letters Patent are hereby corrected as shown below:

Column 1, line 65, "s" should read -- is --.

Column 10, line 43, cancel "-Br" in the formula.

Signed and Sealed this

Nineteenth Day of October 1976

[SEAL]

Attest:

RUTH C. MASON
Attesting Officer

C. MARSHALL DANN
Commissioner of Patents and Trademarks